(12) United States Patent
Russell

(10) Patent No.: US 7,705,313 B1
(45) Date of Patent: Apr. 27, 2010

(54) AMBIENT GAS COMPENSATION IN AN OPTICAL SYSTEM

(75) Inventor: James T. Russell, Bellevue, WA (US)

(73) Assignee: RIC Investments, LLC, Wilmington, DE (US)

( * ) Notice: Subject to any disclaimer, the term of this patent is extended or adjusted under 35 U.S.C. 154(b) by 493 days.

(21) Appl. No.: 11/582,251

(22) Filed: Oct. 17, 2006

Related U.S. Application Data

(60) Provisional application No. 60/727,962, filed on Oct. 18, 2005.

(51) Int. Cl.
*G01J 5/02* (2006.01)

(52) U.S. Cl. .................................. 250/343; 250/339.13

(58) Field of Classification Search .............. 250/484.5, 250/339.08, 339.13, 339.12, 252.1, 343, 250/339.14
See application file for complete search history.

(56) References Cited

U.S. PATENT DOCUMENTS

| | | | | |
|---|---|---|---|---|
| 5,175,596 A | * | 12/1992 | Dick et al. | .................. 356/442 |
| 5,473,162 A | * | 12/1995 | Busch et al. | .............. 250/341.6 |
| 5,578,828 A | * | 11/1996 | Brown et al. | ................. 250/342 |
| 7,157,723 B2 | * | 1/2007 | Colvin et al. | ............. 250/458.1 |
| 7,233,001 B2 | * | 6/2007 | Lievois et al. | .......... 250/339.12 |
| 7,248,357 B2 | * | 7/2007 | Servaites et al. | ............ 356/306 |
| 2002/0026108 A1 | * | 2/2002 | Colvin, Jr. | ................... 600/316 |

* cited by examiner

*Primary Examiner*—David P Porta
*Assistant Examiner*—Faye Boosalis

(57) ABSTRACT

An optical sensor is configured to determine an amount of at least one material in a sample without interference from any of the material of interest present in an ambient environment in which the optical sensing is effected. The optical sensor may include a compensation detector positioned a different distance apart from a source of monitoring radiation than the distance that a primary, measurement detector is positioned from the source. Alternatively, the optical sensor may include an optically transparent material that consumes space within the sensor and, thus, eliminates ambient amounts of a material of interest from at least a portion of an optical pathway through the sensor. A calibration element transmits calibration radiation to one or more detectors of an optical sensor to facilitate correction of any changes in the manner in which the one or more detectors sense radiation. Optical sensing methods are also disclosed, as are calibration methods.

27 Claims, 4 Drawing Sheets

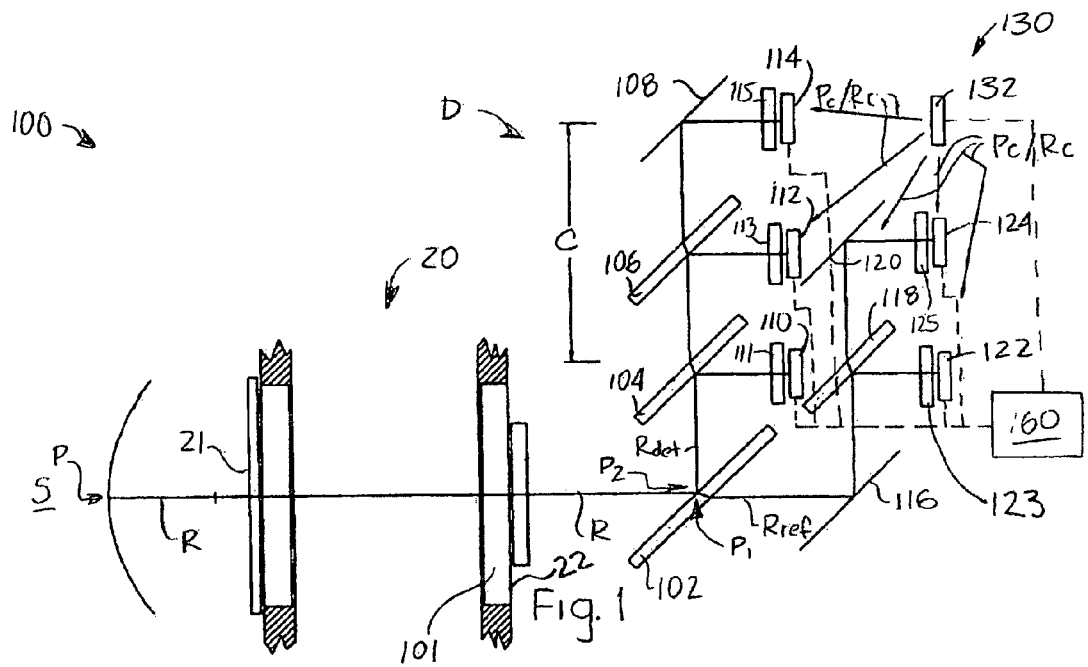
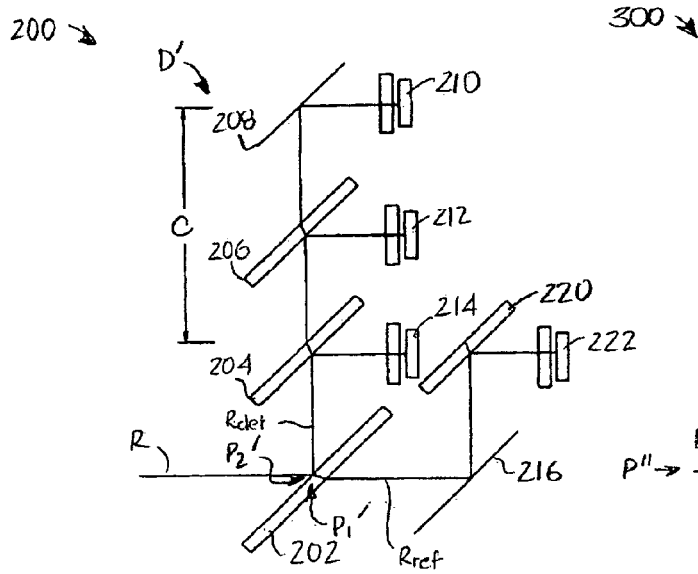
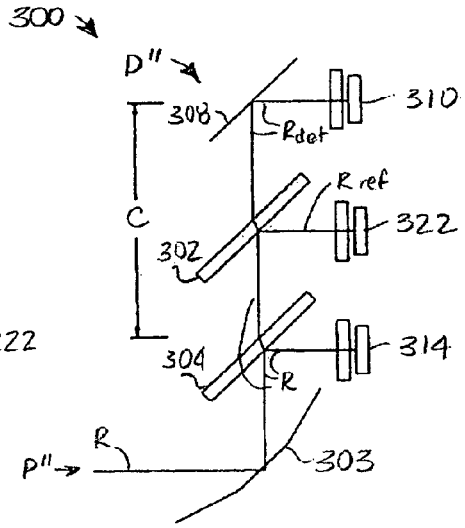
Fig. 1
Fig. 2
Fig. 3

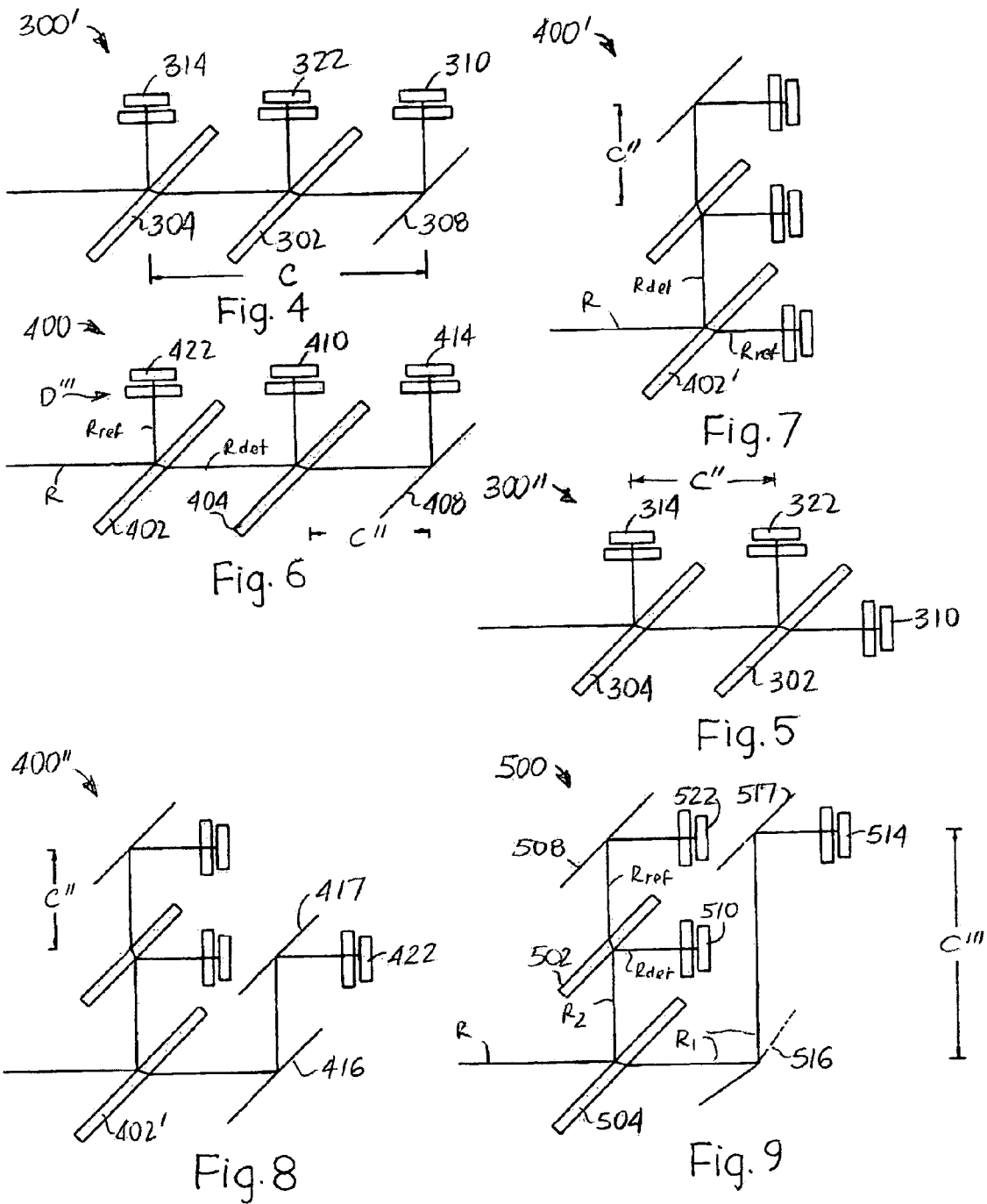

AMBIENT GAS COMPENSATION IN AN OPTICAL SYSTEM

CROSS-REFERENCE TO RELATED APPLICATIONS

This application claims priority under 35 U.S.C. §119(e) from provisional U.S. patent application No. 60/727,962 filed Oct. 18, 2005 the contents of which are incorporated herein by reference.

BACKGROUND OF THE INVENTION

1. Field of the Invention

The present invention relates generally to optical sensing techniques and apparatus, and, more specifically, to techniques and apparatus for obtaining a measurement of at least one material in a sample that is substantially free of ambient gas.

2. Description of the Related Art

Optical sensors have long been used to measure the amount of one or more gases in a sample of interest. Optical sensors have been used in a variety of environments, including respiratory gas monitoring. The operation of many optical sensors is based upon a scientific principle known as "absorbance" or "attenuation" of electromagnetic radiation, such as light or infrared radiation.

The wavelengths of electromagnetic radiation that are absorbed by many materials, including gases, liquids, and solid materials, are well known. These absorbed wavelengths of electromagnetic radiation are known as the "absorption peaks" for their respective materials. Some materials absorb electromagnetic radiation of wavelengths that are not absorbed at all or in significant amounts by other materials that may be present in the same sample. For example, the absorption peak for carbon dioxide is centered at a wavelength of about 4.26 µm, whereas nitrogen, oxygen, and other gases that are typically present in monitored respiration do not absorb radiation at this wavelength. Such an absorption peak is useful for monitoring an amount (e.g., concentration, fraction, etc.) of that material in a sample.

The amount of a particular material in a sample may be determined by directing monitoring radiation, including electromagnetic radiation at the absorption peak for that material in a known intensity, into the sample. If the material of interest is present in the sample, the intensity of the wavelength or wavelengths of monitoring radiation that correspond to the absorption peak will decrease, or become "attenuated." Attenuation may be measured in terms of percent absorbance or optical density (OD). A measure of this decrease in intensity, or "attenuation," of the monitoring radiation may correspond to the amount of the material in the sample.

Because the intensity of the monitoring radiation may also be decreased by factors other than absorption of the monitoring radiation by the material of interest, reference electromagnetic radiation of a different wavelength, which is not absorbed by the material of interest, and of known intensity may be directed along roughly the same optical path and substantially the same distance as those along which the monitoring radiation travels. The intensity of the reference electromagnetic radiation may be detected by a reference sensor and, thus, the decrease in intensity of the reference electromagnetic radiation may be measured. The measured decrease in intensity of the reference electromagnetic radiation may then be used to determine non-absorption decreases in the intensity of the monitoring radiation. Conventionally, any other decreases in monitoring radiation have been attributed to absorption of some of the monitoring radiation by the material or materials of interest.

Unfortunately, existing technologies do not account for the possible presence of a material of interest in the ambient environment around or within a monitor, or eliminate the material of interest from the ambient environment around or within the monitor. As a result, optical measurements of the material of interest may be somewhat inflated, including not only an amount of the material of interest in a sample, but also the amount of that material present under ambient conditions.

SUMMARY OF THE INVENTION

Without limiting its scope, the present invention includes optical sensors that are configured to compensate for the possible presence of a material of interest in the ambient environment through which monitoring radiation passes, optical sensors that eliminate the possibility of a material of interest in the ambient environment from interfering with monitoring radiation, and methods for eliminating error introduced by a material of interest that is possibly present in the ambient environment into an optical measurement of the amount of the material of interest in a sample.

An exemplary embodiment of optical sensor includes a housing with a window for receiving monitoring radiation. The window is positioned along an optical path through the monitor. A primary sensor positioned within the housing senses a portion of the monitoring radiation that passes through the window. A compensation sensor measures another portion of the monitoring radiation, which has a longer path length than the portion of monitoring radiation sensed by the primary sensor. The difference in intensity measured by the primary sensor and the compensation sensor correlates to an amount of ambient gas along at least a portion of the optical path (e.g., within the housing).

Another example of an optical sensor includes a housing with a window positioned to receive monitoring radiation, as well as one or more solid, at least partially transparent elements extending completely between the window and a sensor that detects the monitoring radiation. The solid, at least partially transparent elements may include substantially transparent filler elements, as well as optical elements (e.g., dichroic filters, beam splitters, filters, mirrors, etc.).

An example of a method for compensating for ambient material along an optical path of an optical sensor includes measuring and normalizing (for differences in intensity attributable to windows, dichroic splitters, partially transmissive mirrors, filters, and other known factors) intensities of a particular wavelength of electromagnetic radiation at two locations that require that the analyzed radiation travel different pathlengths, considering the difference in pathlengths between the two detectors, and considering a difference in the normalized intensities, as a function of the difference in the pathlengths.

As another example, an ambient material compensation technique may include exclusion of the ambient material from all or part of the system. For example, solid optically transmissive elements could occupy all of the optical pathways through a detector and, optionally, through a source of electromagnetic radiation.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 1-9 are schematic representations of various examples of optical sensors that include components that facilitate a determination of an amount of a material of interest present in an ambient environment and, thus, of optical sensors that may be used in compensating and correcting for the presence of the material of interest in the ambient environment within which optical sensing is being effected;

DETAILED DESCRIPTION OF THE EXEMPLARY EMBODIMENTS

Figure 10:
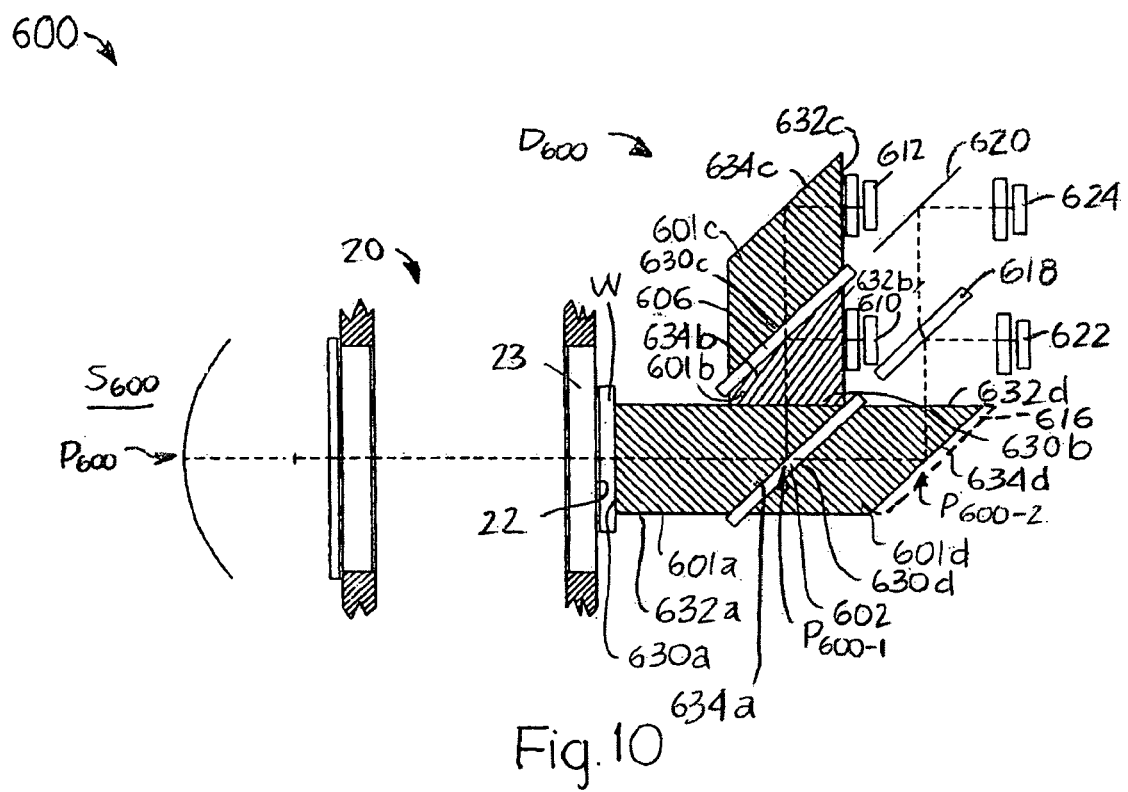
FIG. 10 is a schematic representation of an example of an optical sensor with optical paths that are occupied by solid, optically transmissive elements to prevent introduction of inaccuracies that may be caused by the presence of a material of interest in the ambient environment into a measurement of the material of interest.

FIG. 1 illustrates a first example of an embodiment of optical sensor 100 that incorporates teachings of the present invention. Optical sensor 100 includes a source S of electromagnetic radiation, which is configured to be positioned on one side 21 of a sample cuvette 20, as well as a detection system D configured to be positioned on another (e.g., the opposite) side 22 of sample cuvette 20. Optical sensor 100 may be used to detect one or more gaseous or vapor components of a sample. By way of nonlimiting example, optical sensor 100 may be configured to monitor carbon dioxide and nitrous oxide in a respiratory sample.

When optical sensor 100 is configured for monitoring carbon dioxide, nitrous oxide, or other materials that attenuate electromagnetic radiation in the infrared portion of the spectrum, source S may comprise a source of electromagnetic radiation R of one or more infrared wavelengths. Radiation R is emitted along a path P, which extends from source S to detection system D. When radiation R is used to monitor one or more gaseous or vapor components in a sample, cuvette 20 is positioned along path P, between, source S and detection system D, as illustrated in FIG. 1.

As illustrated, detection system D may include an entrance window 101. Entrance window 101 may include a filter (e.g., integral, laminated thereto, etc.), such as a long pass filter, to prevent certain wavelengths of electromagnetic radiation from entering detection system D.

Detection system D includes a dichroic splitter 102 of a type known in the art, which splits radiation R by wavelength (e.g., a cut-off somewhere between 4.26 µm and 3.681 µm, wavelengths above which cut-off are absorbed by carbon dioxide or nitrous oxide and wavelengths beneath which cut-off are used as a reference or are absorbed by anesthetic agents). One or more wavelengths of radiation R that are used to detect the presence or absence (qualitative) or intensity (quantitative) of one or more components (e.g., $CO_2$, $N_2O$, etc.) of a sample, which is referred to herein as "detection radiation $R_{det}$," are transmitted along subpath $P_1$. One or more other wavelengths of radiation R that are used, among other purposes, as a reference and may also be used to detect the presence, absence, or amount of one or more other materials (e.g., anesthetic agents) in the sample, which are referred to herein, without limitation, as "reference radiation $R_{ref}$," are transmitted along subpath $P_2$. For example, dichroic splitter 102 may reflect wavelengths of radiation R above its cut-off along subpath $P_1$ and transmit wavelengths of radiation R below its cut-off along subpath $P_2$. More specifically, dichroic splitter 102 may be configured to reflect detection radiation $R_{det}$, which includes wavelengths that exceed the cut-off of dichroic splitter 102, and to transmit reference radiation $R_{ref}$, which includes wavelengths below the cut-off.

Detection radiation $R_{det}$, or portions thereof, travel along subpath $P_1$ and its branches to one or more primary detectors 110, 112 and to a compensation detector 114. A partially transmissive mirror 104 and another dichroic splitter 106 are positioned along subpath $P_1$. Additionally, another mirror 108 may be positioned along subpath P1, downstream from dichroic splitter 106.

Partially transmissive mirror 104 reflects or transmits a certain percentage of radiation (e.g., 90% reflected, 10% transmitted, etc.) regardless of wavelength. As shown, partially transmissive mirror 104 may be oriented to direct (e.g., by reflection, as illustrated) some detection radiation $R_1$ to a first detector 110, or sensor, which is configured to sense radiation of wavelengths (e.g., 4.26 µm) that are attenuated by a first material (e.g., carbon dioxide) that may be present in a sample. First detector 110 senses an intensity of at least one wavelength of radiation $R_{det}$. The sensed intensity may be quantified and correlated to a particular amount (e.g., fraction, partial pressure, etc.) of the first material in the sample, as known in the art.

The portion of detection radiation $R_{det}$ that is directed by (e.g., passes through) partially transmissive mirror 104 is directed to dichroic splitter 106, which splits that portion of the detection radiation $R_{det}$ on the basis of wavelength (e.g., at a cut-off between a wavelength, such as 4.26 µm, absorbed by $CO_2$ and a wavelength, such as 4.47 µm, absorbed by $N_2O$, etc.). Dichroic splitter 106 directs specific wavelengths of detection radiation $R_{det}$ (e.g., wavelengths above the cut-off) into a second detector 112 (e.g., by selective reflection). Second detector 112 is configured to sense radiation of one or more wavelengths that are attenuated by a second material that may be present in a sample (e.g., nitrous oxide, or $N_2O$). The sensed intensity of the one or more sensed wavelengths of radiation $R_2$ may be quantified and correlated to a particular amount of the second material in the sample in a manner known in the art.

Wavelengths of detection radiation $R_{det}$ that pass through dichroic splitter 106 (e.g., those below the cut-off) are directed to compensation detector 114. As depicted, these remaining wavelengths of detection radiation $R_{det}$ may be reflected by one or more mirrors 108 prior to reaching compensation detector 114, which may be used to increase the compactness of a transducer (not shown) of which detection system D is a part. Compensation detector 114 is configured to sense the same wavelengths of electromagnetic radiation as either first detector 110 or second detector 112. In the illustrated embodiment, compensation detector 114 is configured to sense the same wavelengths of electromagnetic radiation as first detector 110.

Ambient amounts of one or more gases that are to be detected with optical sensor 100 may absorb some detection radiation $R_{det}$ before detection radiation $R_{det}$ reaches first detector 110 or second detector 112. The amount of attenuation depends, at least in part, upon the pathlength along which the radiation is transmitted before being detected. Since the radiation ($R_1$, $R_3$) sensed by first detector 110 or second detector 112 travels a different distance than the radiation ($R_4$) sensed by compensation detector 114, the amount of a material of interest that is detected by use of compensation detector 114 differs from the amount of the material of interest that is detected with first detector 110 or second detector 112. This difference in pathlength, which is equal to compensation distance C, may be used in conjunction with the differences amounts of a material of interest detected by compensation detector 114 and first detector 110 or second detector 112 to determine the amount of ambient material through which radiation R or a portion thereof has been transmitted.

As it is desired to measure selected gaseous or vapor components with a sample cuvette, the presence of unknown amounts of the same gaseous or vapor components within the detection system will cause an error in the data obtained from the primary detectors. Measurements from the compensation detector combined with measurements from the primary detector or detectors permit the amount of a selected gaseous or vapor component within the detection system, i.e., ambient material, to be determined with greater accuracy. The additional absorbance "seen" by compensation detector of the selected gaseous or vapor component is due to the additional pathlength, the compensation distance C. This additional absorbance measured by the compensation detector can be taken into account, for example, by being subtracted from the measurements made by the primary detection system. Thus, the output or signal from the primary detector or detectors is corrected by the output or the signal from the compensation detector.

Compensation distance C is the difference in the distance between a common fixed point located upstream from detectors 110, 112, 114, such as source S, and first detector 110 or second detector 112 and the distance between the common fixed point and compensation detector 114. As illustrated, compensation distance C is the distance from the point at which subpath $P_1$ intersects partially transmissive mirror 104 to the point at which subpath $P_1$ is reflected by mirror 108, with the distance between partially transmissive mirror 104 and first detector 110 and the distance between mirror 108 and compensation detector 114 being equal. Alternatively, the distance between a common fixed point and compensation detector 114 may be less than the distance between the common fixed point and first detector 110 or second detector 112.

The compensation distance C, which is determined by the physical arrangement of the optical elements and detectors of the detection system, will be different for each optical configuration and may vary slightly between detection systems of the same optical configuration due to manufacturing tolerances. Thus, it is preferable to perform an initial calibration due to the resulting different relative sensitivities of the primary and compensation sensors When the amount of ambient material is known, that amount may be used to correct data obtained by use of first detector 110 or second detector 112 by methods known to one skilled in the art to increase the accuracy of a measurement that has been obtained by using first detector 110 or second detector 112. In an exemplary embodiment, the method for correcting the CO2 as the ambient material, i.e., the material in the space between detectors, is accomplished by determining the difference in the absorbance measured by first detector 110 and compensation detector 114 and using this difference to correct for the CO2 measurement of the first detector. A similar process can be accomplished for second detector 112.

For this calculation to be valid, the relative sensitivities of the primary and compensation sensors, or the ratio of these sensors, must be known. The relative sensitivities can be determined, for example, during the last stages of the manufacturing process by placing the complete system in a non-active atmosphere, e.g., nitrogen or helium, or placed in an evacuated chamber, to remove all absorbing gasses from the system. Then the source is activated. The outputs of all detectors are recorded, and the ratio of the primary and compensating sensors is calculated and recorded on the product. This ratio is the normalizing factor that is applied to the compensating detector signal when a correction for ambient gas is calculated. By doing the calibration in this way, all optical variables are taken into account, including, but not limited to, minor misalignments and losses at each optical element.

Reference radiation $R_{ref}$ or portions thereof pass through dichroic splitter 102 and are transmitted along subpath $P_2$ and its branches, if any, to a reference detector 122 and, optionally, to a detector for sensing one or more anesthetic agents, which is referred to hereinafter as an "agent detector 124." In the illustrated example, a mirror 116 may be positioned along subpath $P_2$ to direct electromagnetic radiation to a partially transmissive mirror 118, which directs a some reference radiation $R_{ref}$ to reference detector 122 (e.g., by reflection, as shown) and the remaining reference radiation $R_{ref}$ to agent detector 124 (e.g., by permitting radiation $R_{ref}$ to pass therethrough). It should be noted that a dichroic splitter may be used in place of partially transmissive mirror 118 if the wavelengths to be detected by reference detector 122 and the wavelength to be detected by agent detector 124 may be separated from one another.

As depicted, another mirror 120 may be positioned between partially transmissive mirror 118 and agent detector 124. One or both of mirrors 116 and 120 may be included to increase the compactness of a transducer (not shown) of which detection system D is a part.

Reference detector 122 is configured to detect an intensity of a known portion of reference radiation $R_{ref}$. Each wavelength of reference radiation $R_{ref}$ (e.g., 3.681 µm, etc.) detected by reference detector 122 is expected to be substantially unattenuated by constituents of a sample to be analyzed and of the ambient environment in which the analysis will take place. Thus, the measured intensity of reference radiation $R_{ref}$ may be compared with the measured intensity of a known portion of detection radiation $R_{det}$ to determine the extent to which factors other than attenuation by a material of interest decreased the intensity of detection radiation $R_{det}$.

Agent detector 124 may be configured to detect an intensity of a known portion of detection radiation $R_{det}$ (e.g., an absorption peak centered at about 3.3 µm), which may be compared with the measured intensity of a known portion of reference radiation $R_{ref}$ to determine the extent to which one or more anesthetic agents or other materials of interest attenuate, or decrease, the intensity of the known portion of detection radiation $R_{det}$.

Partially transmissive mirrors, which are well known in the art, (e.g., partially transmissive mirrors 104 and 118) may have any suitable ratio of reflectivity to transmissivity, as long as the intensities of the different portions of radiation divided thereby are adequate to generate an accurate signal by detectors 110, 112, 114, 122, and 124.

Detectors (e.g., detectors 110, 112, 114, 122, and 124) may comprise any suitable type of optical detection apparatus known in the art. By way of nonlimiting example, lead selenide detectors are useful in detection systems (e.g., detection system D) that incorporate teachings of the present invention.

A narrow pass filter 111, 113, 115, 123, 125 of a known type, which allows only a narrow range of wavelengths of electromagnetic radiation to pass therethrough, may be associated with each detector (e.g., detectors 110, 112, 114, 122, and 124, respectively) in such a way as to control the wavelengths of electromagnetic radiation to which the detector is exposed. Of course, the selectivity of the filter associated with detector depends upon the intended function of that detector (e.g., a reference wavelength, a wavelength absorbed by a material of interest, etc.).

Optical sensor 100 or, more specifically, detectors 110, 112, 114, 122, 124 thereof, may communicate with other electronic components (not shown), including a processing element 160 of a type known in the art (e.g., a microprocessor or microcontroller). Signals that are generated by detectors 110, 112, 114, 122, and 124 upon sensing radiation are manipulated (e.g., amplified, filtered, converted from analog to digital form, etc.), if necessary, and transmitted to processing element 160. Processing element 160 is configured to receive the signals and calculate (e.g., under control of software, firmware, hardware, etc.) a compensation factor based upon the signals (which are indicative of amounts of radiation sensed by first detector 110, compensation detector 114, and reference detector 122), as well as upon the compensation distance C and decreases in the intensity of radiation that are not attributable attenuation by a material of interest.

More specifically, an intensity of the signal received from compensation detector 114 is compared with an intensity of the signal received from the detector 110. A difference between the optical pathlengths to the two detectors 110 and 114 is also considered. In addition, processing element 160 is configured, or programmed, to account for relative proportions of the intensity of the portions of the attenuated signal received by detector 110 and compensation detector 114, as well as other factors that may decrease the intensity of the sensed radiation. The compensation factor may then be used with (e.g., subtracted from, etc.) a measurement of a material of interest that has been calculated by processing element 160 in accordance with known processes to correct for the possible presence of the material of interest in the ambient environment.

A number of other examples of optical detection systems that are configured to compensate for ambient amounts of one or more materials of interest are depicted in FIGS. 2 through 9.

In FIG. 2, an optical sensor 200 is illustrated. Like optical sensor 100, optical sensor 200 includes a source S (see FIG. 1, not shown in FIG. 2) and a detection system D'. Detection system D' is configured to sense two different materials.

Detection system D' includes a dichroic splitter 202 or other similarly functioning element that is positioned to receive radiation R that has been transmitted by source S, through a sample (not shown), and into detection system D'. Dichroic splitter 202 splits radiation R into at least two different wavelengths, directing a portion of radiation R along a first subpath $P_1'$ and another portion of radiation R along a second subpath $P_2'$. More specifically, the portion of radiation R that is directed along first subpath $P_1'$ may include one or more wavelengths of detection radiation $R_{det}$ that are useful in qualitatively or quantitatively detecting an amount of one or more materials in the sample. The portion of radiation R that is directed along second subpath $P_2'$ may include one or more wavelengths of reference radiation $R_{ref}$ that are useful in providing a reference for factors, other than attenuation by the material or materials of interest, that reduce the intensity of radiation $R_{det}$, $R_{ref}$ as it is transmitted from source S to one or more detectors. Although FIG. 2 shows that reference radiation $R_{ref}$ may be transmitted through dichroic splitter 202 and that detection radiation $R_{det}$ may be reflected by dichroic splitter 202, use of a dichroic splitter or similarly functioning element to transmit detection radiation $R_{det}$ and to reflect reference radiation $R_{ref}$ is also within the scope of the present invention.

Detection radiation $R_{det}$ is directed by dichroic splitter 202 toward a partially transmissive mirror 204, which reflects some detection radiation $R_{det}$ to a compensation detector 214. Another portion of detection radiation $R_{det}$ is transmitted through partially transmissive mirror 204 to another dichroic splitter 206. Upon reaching dichroic splitter 206, at least one wavelength of the transmitted detection radiation $R_{det}$ is directed (e.g., by reflection, as illustrated) to a detector 212, while other wavelengths of detector radiation $R_{det}$ are directed (e.g., by transmission through dichroic splitter 206, as depicted) to another detector 210. As illustrated, one or more mirrors or other optical elements may be positioned and oriented along a subpath $P_1'$ to direct detection radiation $R_{det}$ or portions thereof to desired locations. For example, a mirror 208 may be positioned between dichroic splitter 206 and detector 210.

Although detector 210 is positioned further along subpath $P_1'$ than compensation detector 214, compensation distance C is the difference in the distance between compensation detector 214 and a common fixed point located upstream of detectors 214 and 210 and the distance between detector 210 and the common fixed point. Signals from detectors 210 and 214 may be used to provide an accurate measure of the amount of the material of interest in a sample, such as in the manner described in reference to FIG. 1.

Reference radiation $R_{ref}$ is directed along subpath $P_2'$ to a reference detector 222. As illustrated, one or more mirrors 216, 220 may be positioned along subpath $P_2'$ to direct reference radiation $R_{ref}$ to reference detector 222.

FIG. 3 depicts another embodiment of optical sensor 300 of the present invention. Optical sensor 300, which is configured to detect a single material, includes a source S (see FIG. 1, not shown in FIG. 3) and a detection system D".

Detection system D" includes a single path P", along which radiation R is directed to a compensation detector 314, a reference detector 322, and a primary detector 310.

As illustrated, detection system D" also includes a mirror 303 positioned along path P, upstream from the locations of detectors 314, 322, 310. Mirror 303 may be included to impart optical sensor 300 with a particular, desired configuration.

A portion of radiation R is directed (e.g., by reflection, as shown) to compensation detector 314 by a partially transmissive mirror 304 positioned on path P. Another portion of radiation R is directed (e.g., by being transmitted through partially transmissive mirror 304, as illustrated) to a dichroic splitter 302 or other similarly functioning element. Dichroic splitter 302 is positioned (e.g., along path P) and oriented to direct (e.g., by reflection, as shown) one or more wavelengths of reference radiation $R_{ref}$ to reference detector 322 and to direct (e.g., by transmission, as depicted) one or more wavelengths of detection radiation $R_{det}$ to detector 310. One or more mirrors 308 may be positioned along path P, downstream from dichroic splitter 302, and oriented so as to direct detection radiation $R_{det}$ to a desired location; i.e., the location of detector 310.

A compensation distance C of detection system D" is equal to the difference in the distance between compensation detector 314 and a common fixed point located upstream of detectors 314 and 310 and the distance between detector 310 and the common fixed point. Signals from detectors 310 and 314 may be used to provide an accurate measure of the amount of the material of interest in a sample, such as in the manner described in reference to FIG. 1.

The variation of optical sensor 300' shown in FIG. 4 differs from optical sensor 300 only in that optical sensor 300' lacks a mirror 303 upstream from detectors 314, 322, and 310.

Another variation of optical sensor 300", which is depicted in FIG. 5, differs from optical sensor 300' only in that it lacks a mirror 308 downstream from dichroic splitter 302 and has a shorter compensation distance C". This is because the distance from partially transmissive mirror 304 to detector 310 in optical sensor 300" is shorter than the corresponding distance in optical sensor 300'.

FIG. 6 illustrates another embodiment of optical sensor 400, which is configured much like optical sensor 300', but with the components thereof in different positions. Specifically, upon entering detection component D''' of optical sensor 400, radiation R first encounters a dichroic splitter 402, which separates reference radiation $R_{ref}$ from detection radiation $R_{det}$. Reference radiation $R_{ref}$ is transmitted (e.g., by reflection, as illustrated) to a reference detector 422, while detection radiation $R_{det}$ is transmitted (e.g., by being transmitted through dichroic splitter 402, as shown) to a partially transmissive mirror 404. Partially transmissive mirror 404 directs (e.g., by reflection, as depicted) a portion of detection radiation $R_{det}$ to a primary detector 410, while another portion of detection radiation $R_{det}$ is directed (by transmission through partially transmissive mirror 404) to a mirror 408, which then reflects that portion of detection radiation $R_{det}$ to a compensation detector 414.

The variation of optical sensor 400' shown in FIG. 7 is arranged much like optical sensor 400, but with a dichroic splitter 402' that is in reversed orientation relative to dichroic splitter 402. Thus, reference radiation $R_{ref}$ may be transmitted through dichroic splitter 402', while detection radiation $R_{det}$ may be reflected by dichroic splitter 402'.

The components of another variation of optical sensor 400", which is depicted in FIG. 8, are arranged and oriented like the corresponding elements of optical sensor 400', with the only exception being the inclusion of one or more mirrors 416, 417 between dichroic splitter 402' and reference detector 422 to effectively increase the pathlength between dichroic splitter 402' and reference detector 422.

FIG. 9 illustrates another embodiment of optical sensor 500 that incorporates teachings of the present invention. Optical sensor 500 includes a partially transmissive mirror 504 that transmits a portion $R_1$ of radiation R and reflects another portion $R_2$ of radiation R. The portion $R_1$ of radiation R that is transmitted through partially transmissive mirror 504 is directed to a compensation detector 514. Portion $R_1$ may also be reflected by one or more mirrors 516, 517 as it is transmitted to compensation detector 514 to increase compensation distance C'''. Portion $R_2$ is directed to a dichroic splitter 502, which directs detection radiation $R_{det}$ to a primary detector 510 (e.g., by reflection, as illustrated) and reference radiation $R_{ref}$ to a reference detector 522 (e.g., by transmission through dichroic splitter 502, as depicted). A mirror 508 may be included to direct reference radiation $R_{ref}$ to reference detector 522.

Turning now to FIG. 10, an example of another embodiment of optical sensor 600 that incorporates teachings of the present invention is illustrated. Optical sensor 600 is substantially or completely free of ambient levels of one or more monitored gases. For example, and without limiting the scope of the present invention, optical sensor 600 includes transparent elements 601a, 601b, 601c, etc., that are positioned along an optical path $P_{600}$ that extends from a source $S_{600}$ to a detection system $D_{600}$ of optical sensor 600, and through detection system $D_{600}$.

Transparent elements 601a, 601b, 601c, etc., may be solid structures. Each transparent element 601a, 601b, 601c, etc., has a known, quantifiable transparency to each wavelength of radiation to be sensed by one or more components of detection system $D_{600}$. The transparency of the material of each solid transparent element 601a, 601b, 601c, etc., as well as the length of a portion of path $P_{600}$ extending through each transparent element 601a, 601b, 601c, etc., may be used along with the percentage and intensity of radiation detected by one or more components of detection system $D_{600}$ to determine the amount of one or more substances (e.g., gases, vapors, etc.) in a sample.

Transparent elements 601a, 601b, 601c, etc., may be formed from a variety of suitable materials, including but not limited to sapphire, silicon, germanium, ZnS, ZnSe, calcium fluoride, and the like. If any of transparent elements 601a, 601b, 601c, etc., is formed from a material that has an index of refraction of about 1.22 or less, a combination of transparent elements 601a, 601b, 601c, etc., and air gaps may be included along path $P_{600}$ of detection system $D_{600}$. If a transparent element 601a, 601b, 601c, etc., is formed from a material with a greater refractive index and an air gap is present down-path from that transparent element 601a, 601b, 601c, etc., a portion of the radiation may be totally internally reflected (TIR) within the transparent element 601a, 601b, 601c, etc., and, thus, not sensed, reducing the accuracy of measurements that may be optically obtained with detection system $D_{600}$.

Detection system $D_{600}$ includes a window W, which is configured to be positioned adjacent to a window 23 on one side 22 of a sample cuvette 20 and along a path $P_{600}$ that extends through sample cuvette 20. An end 630a of a first transparent element 601a is positioned adjacent to window W, also along path $P_{600}$. First transparent element 601a includes one or more side surfaces 632a, as well as an angled end 634a opposite from end 630a. Angled surface 634a is oriented obliquely relative to the length of first transparent element 601a and to the direction in which path $P_{600}$ extends. A dichroic splitter 602 is positioned in contact with angled end 634a. Dichroic splitter 602 splits path $P_{600}$ into two subpaths $P_{600-1}$ and $P_{600-2}$.

A second transparent element 601b is positioned along subpath $P_{600-1}$, with an end 630b in contact with a side surface 632a of first transparent element 601a. An opposite end 634b of second transparent element 601b is angled, with the surface being oriented obliquely relative to a length of second transparent element 601b and to the direction in which subpath $P_{600-1}$ extends. A dichroic splitter 606 is positioned in contact with end 634b. A first detector 610 is positioned adjacent to a side surface 632b of second transparent element 601b, and senses at least one wavelength of radiation that is reflected by dichroic splitter 606.

A third transparent element 601c is also oriented along subpath $P_{600-1}$, on an opposite side of dichroic splitter 606 from second transparent element 601b, with an end 630c in contact with dichroic splitter 606. Thus, third transparent element 601c receives wavelengths of radiation that pass through dichroic splitter 606. The surface at an opposite end 634c of third transparent element 601c is oriented obliquely relative to subpath $P_{600-1}$ and is either reflective, as illustrated, or has a mirror positioned adjacent thereto so as to direct radiation into a second detector 612 positioned adjacent to a side surface 632c of third transparent element 601c.

Detection system $D_{600}$ may optionally include a fourth transparent element 601d along a portion of subpath $P_{600-2}$. An end 630d of such a fourth transparent element 601d may be positioned in contact with an opposite surface of dichroic splitter 602 from the surface next to which end 634a of first transparent element 601a is positioned. Thus, fourth transparent element 601d receives radiation that passes through dichroic splitter 602. The radiation may travel through fourth transparent element 601d until reaching the opposite end 634d thereof, which is either reflective, as shown, or has a mirror positioned adjacent thereto. The radiation may then be reflected out of a side surface 632d of fourth transparent element 601d, changing the direction in which subpath $P_{600-2}$ extends.

Upon exiting fourth transparent element 601d, subpath $P_{600-2}$ encounters a partially transmissive mirror 618, by which some radiation is reflected to a third detector 622 (e.g., a reference detector) and other radiation passes through to a mirror 620, which reflects that radiation to another detector 624 (e.g., a detector configured to sense one or more wavelengths of radiation that are absorbed by one or more vaporized anesthetic agents). Optical elements, such as dichroic splitters 602, 606, partially transmissive mirrors 618, mirrors, filters (e.g., narrow pass filters), and the like may be secured to transparent elements 601a, 601b, 601c, etc., and two or more transparent elements 601a, 601b, 601c, etc., may be secured to one another by any suitable technique. As a non-limiting example, an optically acceptable adhesive, or glue, may be used.

In an exemplary embodiment of the present invention, the refractive index of the adhesive is about the same as the refractive index of the material or materials from which transparent elements 601a, 601b, 601c, etc., are formed. For example, the indices of refraction of many optically acceptable adhesives are about 1.45 to about 1.6. As most adhesives are organic in nature, they may absorb significant amounts of radiation in the mid infrared range of wavelengths, which may interfere somewhat with the intensity of one or more detected signals. Accordingly, it may be necessary to account for the affects of adhesive on the wavelength or wavelengths of radiation sensed by one or more of detectors 610, 612, 622, 624. Alternatively, if very thin bond lines are employed (e.g., bond lines having thicknesses on the order of a few microns), the amount of radiation absorbed by the adhesive will be small, perhaps infinitesimal, and accordingly such bonding material may be used with any index material.

In addition to the mirrors, filters, and detectors that have been described above, an optical sensor may include a calibration component 130, which is configured to facilitate periodic monitoring of the sensitivities of at least compensation detector 114 and its corresponding primary detector 110 or 112 and, if necessary, periodic recalibration of one or more detectors 110, 112, 114, etc., or compensation for variations in the sensitivities of one or more detectors 110, 112, 114, etc. Of course, calibration component 130 may also be used with optical sensors that are not within the scope of the present invention.

An example of a calibration component 130 may include a calibration source 132, such as a light-emitting diode (LED) that generates and emits electromagnetic radiation, which is referred to herein as "calibration radiation $R_c$," of at least one wavelength (e.g., radiation of near-infrared wavelengths, such as 840 nm) that will be detected by one or more of detectors 110, 112, 114, 122, and 124. Even though all detectors are calibrated, in situ, during manufacture, the effective sensitivity of one or more detectors may change with time. The change may be due, for example, to contamination on the detector surface, or on the filters, mirrors, splitters, or other optical elements in the optical path. The change may also be due to aging effects in the detector or amplifier circuits and other analog electronic components or circuits that are unique to each particular detector channel. The calibration elements provide a correction for any such changes.

Figure 12:
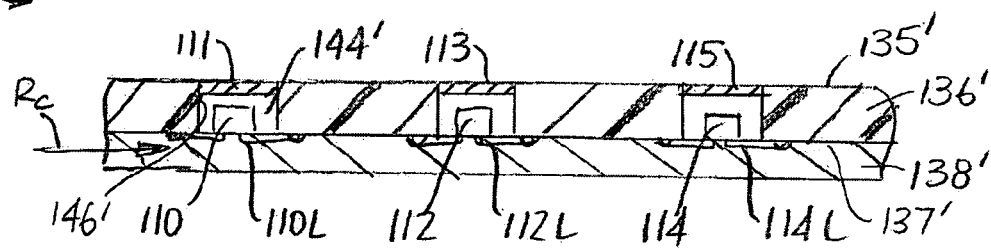
Figure 13:
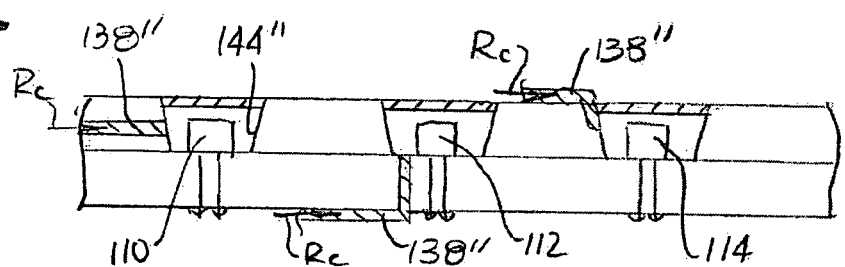

Calibration radiation $R_c$ emitted by calibration source 132 is transmitted to detector 110, 112, 114, 122, 124 (FIG. 1) along a calibration path $P_c$. Each calibration path $P_c$ may comprise an optically transmissive element that channels electromagnetic radiation to a detector 110, 112, 114, 122, 124. Examples of calibration component configurations are illustrated in FIGS. 11-13.

Figure 11:
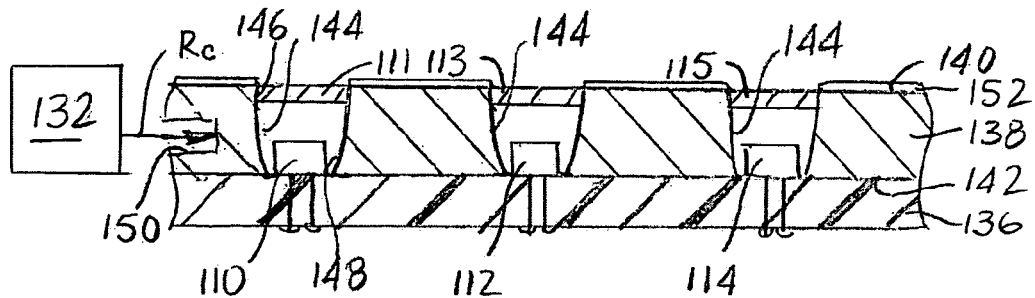
FIGS. 11-13 are cross-sectional depictions of various examples of optical detection apparatus that include calibration components.

The calibration component 130 shown in FIG. 11 includes a carrier substrate 136 by which detectors 110, 112, 114 (detectors 122, 124 have not been illustrated for the sake of simplicity and because an optical sensor according to the present invention need not include more than two detectors) are carried. By way of example only, detectors 110, 112, 114 may be electrically connected and secured to carrier substrate 136. If desired, carrier substrate 136 may be temperature-controllable to facilitate optimization of detection conditions (e.g., sensor temperatures).

An optical substrate 138 is associated with carrier substrate 136 in such a way as to distribute calibration radiation $R_c$ to detectors 110, 112, 114. Thus, optical substrate 138 serves as a so-called "light pipe." Optical substrate 138 may be formed from a material that will transmit calibration radiation $R_c$ but may be substantially opaque to the wavelengths of electromagnetic radiation (e.g., infrared radiation having wavelengths of about 3 μm or greater) that are used to sense one or more materials. For example, optical substrate 138 may be fabricated from a material that optically transmits calibration radiation $R_c$ but does not permit radiation directed toward one detector 110, 112, 114 to be inadvertently transmitted, or leaked, to another detector 110, 112, 114, a phenomenon which is also referred to as "cross-talk." By way of nonlimiting example, plastic, such as polymethylmethacrlate (PMMA), polycarbonate, or polyvinyl, may be used to form optical substrate 138, as many plastics are opaque to mid-infrared wavelengths (e.g., about 2 μm to about 6 μm) of electromagnetic radiation. Alternatively, the material from which optical substrate 138 is fabricated may not itself provide a desired level of opacity to mid-infrared wavelengths or other electromagnetic radiation, but may be impregnated with one or more dyes that will absorb wavelengths of electromagnetic radiation that are not to be transmitted through or by optical substrate 138 without absorbing a significant enough portion of calibration radiation $R_c$, to interfere with calibration of an optical detector.

As illustrated, optical substrate 138 includes a top surface 140 and a bottom surface 142, as well as openings 144 that extend from top surface 140 to bottom surface 142. Each opening 144 is alignable with a detector 110, 112, 114. Detector 110, 112, 114 may merely be exposed to an opening 144, or it may protrude somewhat into opening 144. In the illustrated example, the upper portion 146 of each opening 144, which is located closest to top surface 140 of optical substrate 138, is larger than the lower portion 148 of that opening 144, which is located closest to bottom surface 142 of optical substrate 138. This configuration facilitates retention of a narrow band filter 111, 113, 115 within top portion 146, as well as spacing of narrow pass filter 111, 113, 115 apart from a radiation sensing surface of each detector 110, 112, 114.

Optical substrate 138 may also include a receptacle 150 into which calibration radiation $R_c$ is directed.

Upper surface 140 of optical substrate 138 may optionally include a coating 152 of a material that is opaque to ambient or stray electromagnetic radiation to prevent exposure of detectors 110, 112, 114 to such radiation, which could interfere with or otherwise reduce the accuracy of signals generated by detectors 110, 112, 114. Examples of coating 152 materials include, but are not limited to, aluminum, aluminum oxide, paints, and other opaque materials.

An alternative embodiment of calibration component 130', depicted in FIG. 12, includes a carrier substrate 136', such as a circuit board, with an upper surface 135' and a lower surface 137'. One or more openings 144' extend through carrier substrate 136'. A detector 110, 112, 114 is positioned within each receptacle 144', and is secured and electrically connected (e.g., by leads 110L, 112L, 114L) to terminals that are carried by lower surface 137' of carrier substrate 136'. A narrow pass filter 111, 113, 115 is also positioned within or over each opening 144', at or near a top portion 146' thereof, which is located adjacent to upper surface 135' of carrier substrate 136'. An optically transmissive element 138', which may be configured as a sheet formed from a material of the type described above with respect to the optical substrate 138 shown in FIG. 11, is positioned against and, optionally, secured to lower surface 137' of carrier substrate 136', such that calibration radiation $R_c$ transmitted therethrough will be transmitted into each opening 144' of carrier substrate 136' and, thus, sensed by the detector 110, 112, 114 within that opening 144'.

FIG. 13 depicts another embodiment of calibration component 130'', in which calibration radiation $R_c$ is transmitted along discrete optical elements 138'', such as optical fibers, that extend to chambers 144'' within which detectors 110, 112, 114 are contained. While optical elements 138'' are depicted as entering chambers 144'' from three different locations, in practice any location or combination of locations may be employed.

As an example, calibration component 130, 130', 130'' may be used to ensure that the sensitivities of detectors 110 and 114 are within predetermined limits (e.g., about one percent, etc.) over time, despite variations in temperature and other factors. This may be accomplished when the ratio or ratios of the sensitivities of detectors 110 and 114 are known at the time optical sensor 100 (FIG. 1) is manufactured. That knowledge serves as a reference point for identifying any variations in the sensitivities of detectors 110 and 114 when calibration radiation $R_c$ from a single calibration source 132 is transmitted to and sensed by detectors 110 and 114 at the same time.

Signals that are generated by detectors 110 and 114 upon sensing calibration radiation $R_c$ may be evaluated on a continuous or intermittent basis.

Calibration radiation $R_c$ may be pulsed at a rate that differs from (e.g., is faster than, slower than, etc.) the rates at which other signals in the system (i.e., optical sensor 100 (FIG. 1)) are pulsed. The pulsation of calibration radiation $R_c$ results in a similar pulsation of signals that are generated by detectors 110 and 114 as they sense calibration radiation $R_c$. Such signal pulsation may be used to facilitate distinction, by a processing element 160 that receives signals from detectors 110, 114, between signals that are generated as calibration radiation $R_c$ is sensed and signals that are generated as one or more materials are sensed.

In addition, or as an alternative, calibration radiation $R_c$ may be intermittently emitted by calibration source 132. For example, when optical sensor 100 is used to monitor one or more materials in the respiration of a subject, signals that are useful in determining the amounts of one or more materials present in the respiration of a subject are generated during exhalation, or expiration. The amounts of gases, vapors, or other materials that are typically measured during expiration are much lower during inspiration. Consequently, if radiation R is not transmitted through a sample or into detector component D during inhalation, or inspiration, by the subject, the signals that are generated by detectors 110 and 114 when they sense calibration radiation $R_c$ during inhalation may be intermittently evaluated with little or no interference.

Of course, calibration radiation $R_c$ may be transmitted to any combination of detectors 110, 112, 114, 122, 124 (see FIG. 1) of optical sensor 100 so that their sensitivities can be monitored to facilitate their recalibration. Use of a calibration system 130 in this manner by a processing element 160 associated with detectors 110, 112, 114, 122, 124 and configured to calculate, from signals generated by detectors 110, 112, 114, 122, 124, the amount of one or more materials of interest present in a sample may improve the accuracy of measurements that are obtained when optical sensor 100 is used.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed:

1. An optical sensor, comprising:
   a primary detector adapted to detect a portion of an attenuated signal indicative of a concentration of at least one material in a sample;
   a compensation detector adapted to detect another portion of the attenuated signal; and
   a processing element in communication with and configured to receive signals from the primary detector and the compensation detector, wherein the processing element is programmed to compare a signal received from the compensation detector to a signal received from the primary detector and based thereon determine an ambient amount of the at least one material in an environment within or around the optical sensor.

2. The optical sensor of claim 1, wherein the processing element is programmed to (a) compare an intensity of the signal received from the compensation detector to an intensity of the signal received from the primary detector; and (b) account for a difference between a path length of the portion of the attenuated signal and a path length of the another portion of the attenuated signal in determining the ambient amount of the at least one material.

3. The optical sensor of claim 2, wherein the processing element is further programmed to account for relative proportions of the intensity of the portions of the attenuated signal received by the compensation detector and the primary detector.

4. The optical sensor of claim 3, wherein the processing element is also programmed to account for at least one other factor that decreases an intensity of the attenuated signal received by the compensation detector of the primary detector.

5. The optical sensor of claim 1, further comprising a reference detector adapted to detect a reference signal.

6. The optical sensor of claim 1, further comprising a calibration component associated with the primary detector and the compensation detector.

7. The optical sensor of claim 6, wherein the calibration component includes:
   a source of calibration radiation; and
   means for transmitting the calibration radiation from the source to at least the primary detector and the compensation detector.

8. The optical sensor of claim 7, wherein the means for transmitting comprises a film or sheet of material that will transmit the calibration radiation.

9. The optical sensor of claim 8, wherein the means for transmitting is opaque to wavelengths of electromagnetic radiation that are to be detected by at least the primary detector and the compensation detector.

10. The optical sensor of claim 7, wherein the source is configured to emit the calibration radiation in a pulsed manner.

11. The optical sensor of claim 1, wherein the compensation detector is configured to sense same wavelengths of electromagnetic radiation as the primary detector, and wherein a path length of the another portion of the attenuated signal received by the compensation detector is different from a path length of the portion of the attenuated signal received by the primary detector.

12. The optical sensor of claim 1, wherein a path length of the another portion of the attenuated signal is longer than a path length of the portion of the attenuated signal.

13. An optical sensor, comprising:
   a housing including at least one window for receiving from a sample at least one optical signal indicative of an amount of at least one material within the sample;
   at least two detectors within the housing for receiving different portions the at least one optical signal along different optical paths having different lengths; and
   at least one transparent element within the housing, the at least one transparent element being separated from the sample and positioned along one optical path of the different optical paths between the window and the at least one detector, the at least one transparent element resulting in no ambient amount of the at least one material being present along the one optical path between the window and the at least one detector.

14. The optical sensor of claim 13, wherein the at least one transparent element comprises at least one transparent solid fill element.

15. The optical sensor of claim 14, further comprising at least one optical element along the optical path, positioned against an end of the at least one transparent solid fill element.

16. The optical sensor of claim 15, wherein the at least one optical element is sandwiched between a pair of transparent solid fill elements.

17. An optical sensor, comprising:
   a primary detector adapted to detect a portion of an attenuated signal indicative of a concentration of at least one material in a sample produced by transmitting electromagnetic radiation from a source of electromagnetic radiation through the sample;
   a reference detector; and
   a calibration component associated with the primary detector and the reference detector configured to facilitate monitoring the sensitivity of one or both of the primary detector and the reference detector, wherein the calibration component includes a source of calibration radiation separate from the source of electromagnetic radiation and means for transmitting the calibration radiation from the source of calibration radiation to at least the primary detector and the reference detector.

18. The optical sensor of claim 17, wherein the means for transmitting comprises a film or sheet of material that will transmit the calibration radiation.

19. The optical sensor of claim 18, wherein the means for transmitting is opaque to wavelengths of electromagnetic radiation that are to be detected by at least the primary detector and the compensation detector.

20. The optical sensor of claim 17, further comprising:
   a compensation detector adapted to detect another portion of the attenuated signal; and
   a processing element in communication with and configured to receive signals from the primary detector and the compensation detector, wherein the processing element is programmed to compare a signal received from the compensation detector to a signal received from the primary detector and based thereon determine an ambient amount of the at least one material in an environment within or around the optical sensor.

21. The optical sensor of claim 17, wherein the source of calibration radiation and the source of electromagnetic radiation are pulsed at different rates.

22. An optical sensing technique, comprising:
   sensing a first portion of an attenuated signal having a wavelength absorbed by at least one material of interest to determine an amount of the material present in a sample; and
   sensing a second portion of the attenuated signal to determine an amount of the material present in an ambient environment in which the acts of sensing are being effected.

23. The optical sensing technique of claim 22, further comprising determining the amount of material present in the ambient environment by (a) considering a difference between the first and second portions of the attenuated signal; and (b) considering a difference in pathlengths of the first and second portions of the attenuated signal.

24. The optical sensing technique of claim 23, wherein determining also includes considering at least one other factor that causes a decrease in intensity of the attenuated signal or a portion thereof.

25. A method for calibrating an optical sensor configured to receive pulsed electromagnetic radiation at a first pulse rate, comprising the acts of:
   transmitting calibration radiation at a second pulse rate to at least one detector of the optical sensor, wherein the first pulse rate is different from the second pulse rate, the at least one detector being adapted to detect a portion of an attenuated signal indicative of a concentration of at least one material in a sample;
   comparing a calibration signal generated by the at least one of detector to an expected signal generated by the at least one detector; and
   altering a subsequent measurement signal based on a difference between the calibration signal and the expected signal.

26. The method of claim 25, wherein transmitting is effected intermittently.

27. The method of claim 25, wherein transmitting is effected as a continuous pulse.

* * * * *